US008008087B1

(12) United States Patent
Shalyt et al.

(10) Patent No.: US 8,008,087 B1
(45) Date of Patent: Aug. 30, 2011

(54) ANALYSIS OF SILICON CONCENTRATION IN PHOSPHORIC ACID ETCHANT SOLUTIONS

(75) Inventors: Eugene Shalyt, Washington Township, NJ (US); Julia Tyutina, Bayonne, NJ (US); Peter Bratin, Flushing, NY (US)

(73) Assignee: ECI Technology, Inc., Totowa, NJ (US)

( * ) Notice: Subject to any disclaimer, the term of this patent is extended or adjusted under 35 U.S.C. 154(b) by 0 days.

(21) Appl. No.: 12/661,968

(22) Filed: Mar. 25, 2010

(51) Int. Cl.
*G01N 33/00* (2006.01)
(52) U.S. Cl. ............................ 436/72; 436/124; 436/125
(58) Field of Classification Search .................... 436/72, 436/124, 125
See application file for complete search history.

(56) References Cited

U.S. PATENT DOCUMENTS 6,890,758 B2 * 5/2005 Shalyt et al. .................. 436/163
2009/0229995 A1 * 9/2009 Shalyt et al. ............... 205/778.5
* cited by examiner

*Primary Examiner* — Jill Warden
*Assistant Examiner* — Dwan A Gerido
(74) *Attorney, Agent, or Firm* — D. Morgan Tench

(57) ABSTRACT

Low concentrations of silicon in an etchant solution are analyzed by adding a predetermined concentration of fluoride ions to a test solution comprising a predetermined volume of the etchant solution, and measuring the concentration of fluoride ions in the test solution. Reaction with silicon ions in the test solution reduces the concentration of fluoride ions, which are present in stoichiometric excess, so that the silicon concentration of the etchant solution can be calculated from the difference between the predetermined and measured concentrations of fluoride ions in the test solution. The method is especially suited for analysis of silicon nitride etchants comprising a high concentration of phosphoric acid.

8 Claims, 4 Drawing Sheets

ANALYSIS OF SILICON CONCENTRATION IN PHOSPHORIC ACID ETCHANT SOLUTIONS

BACKGROUND OF THE INVENTION

1. Field of the Invention

This invention is concerned with analysis of semiconductor processing solutions, particularly with determination of silicon concentration in silicon wafer etchant solutions.

2. Description of the Related Art

Etching processes are critical to fabrication of both circuitry and semiconductor devices on silicon integrated circuit (IC) chips. In one process, a silicon nitride ($Si_3N_4$) mask on a layer of silicon dioxide ($SiO_2$) is patterned etched to expose the underlying silicon/silicon dioxide layer, which is then locally oxidized at high temperature (800-1200° C.) to produce thicker insulating $SiO_2$ in unmasked areas to electrically isolate subsequently formed MOS (metal oxide semiconductor) transistors. The $Si_3N_4$ mask can withstand the high temperature but requires a strong etchant operated at high temperature (>150° C.). The silicon nitride etching process must be closely controlled to provide complete removal of the silicon nitride mask material without excessive etching of the underlying silicon dioxide layer. In particular, it is important to control the etch rate of silicon nitride relative to that of silicon dioxide.

The silicon nitride etchant is generally a concentrated solution of phosphoric acid (85 wt. %) and is operated at a temperature above 150° C. (typically 165° C.). The etch rate of silicon nitride and the selectivity with respect to silicon dioxide in this etchant solution depend strongly on the concentration of silicon ions, which are derived from the etching process and accumulate in the etchant solution with use. Silicon ions reduce the etch rates of both silicon nitride and silicon dioxide in the phosphoric acid etchant but tend to improve the selectivity. It is important that the change in the etch rates and selectivity resulting from accumulation of silicon ions be taken into account to optimize the silicon nitride etching process but available methods for determining the silicon concentration in concentrated phosphoric acid solution are inadequate.

Conventional methods of determining the silicon concentration in aqueous solutions involve reaction of silicon ions with ammonium molybdate to form the ammonium silicomolybdate salt, which is a yellow solid. This reaction is the basis for measuring silicon concentration by a variety of approaches, including those based on gravimetric, spectroscopic, electrochemical and ion chromatography methods. However, ammonium molybdate also reacts with phosphate ions to form an analogous compound that interferes with silicon concentration determinations based on ammonium silicomolybdate. Such interference precludes use of methods based on the ammonium silicomolybdate salt to determine the silicon concentration in silicon nitride etchant solutions containing high concentrations of phosphoric acid.

More sophisticated methods, based on atomic absorption analysis or inductively coupled plasma-atomic emission spectroscopy, for example, are available for analysis of silicon in concentrated phosphoric acid solution. However, such methods require equipment that is large, complex, expensive and costly to maintain, and are not amenable to automation and on-line use.

As described in U.S. Pat. No. 7,351,349 to Shekel et al. (issued 1 Apr. 2008), near infrared (NIR) spectroscopy may be used to detect fluoride species in some silicon dioxide etchant, surface preparation and cleaning solutions. However, available NIR spectroscopic methods and devices do not provide sufficient sensitivity for analysis of small concentrations of silicon in silicon nitride etchant solutions.

European Patent Application No. EP 1724824 A2 to Watatsu et al. (filed 12 May 2006) describes a method for analysis of silicon concentration in silicon nitride etchant solutions comprising concentrated phosphoric acid. In this method, HF added as concentrated hydrofluoric acid to the hot phosphoric acid etchant solution reacts with the silicon to form gaseous $SiF_4$, which is hydrolyzed and detected via a change in conductivity of an aqueous solution. This method is cumbersome and time consuming, involves handling a hazardous gas ($SiF_4$) and is not readily amenable to automation.

There is a need for an effective method of measuring low concentrations of silicon in silicon nitride etchant solutions so that the silicon nitride etch rate and selectivity can be controlled to improve quality and yield of semiconductor IC chips. Preferably, the method would provide accurate results within a short time frame using inexpensive equipment, and would be amenable to automation and on-line process control. Environmental impact of the method is also an important consideration.

SUMMARY OF THE INVENTION

The invention provides a method and an apparatus suitable for determining the silicon concentration in a silicon nitride etchant solution containing a high concentration of phosphoric acid. In the method of the invention, a predetermined concentration of fluoride ions is added to a test solution comprising a predetermined volume of the etchant solution, preferably diluted with a predetermined volume of water, and the concentration of fluoride ions in the test solution is measured. Silicon ions present in the test solution react with the added fluoride ions so as to reduce the measured concentration of fluoride ions. The predetermined concentration of fluoride ions added to the test solution is chosen to be in stoichiometric excess relative to the silicon ions in the test solution so that the silicon concentration in the etchant solution can be calculated from the difference in the predetermined and the measured concentrations of fluoride ions in the test solution. The fluoride ion concentration is preferably measured using a fluoride ion specific electrode (ISE). The invention may also be used to determine the silicon concentration in etchant solutions for other materials than silicon nitride, silicon dioxide, for example, including etchant solutions that do not contain phosphoric acid.

The apparatus of the invention, which enables automated application of the method of the invention for on-line determination of the silicon concentration in an etchant solution, comprises: an analysis cell containing a test solution comprising a predetermined volume of the etchant solution and a predetermined concentration of fluoride ions; a means of providing the predetermined volume of the etchant solution; a means of adding the predetermined concentration of fluoride ions to the test solution; a means of measuring the concentration of fluoride ions in the test solution; and a computing device having a memory element with a stored algorithm operative to effect, via appropriate mechanical and electrical interfacing, at least the basic steps of the method of the invention. The means of measuring the concentration of fluoride ions in the test solution preferably comprises a fluoride ion specific electrode (ISE) in contact with the test solution, a reference electrode in contact with the test solution, and a voltmeter for measuring the potential of the fluoride ISE relative to the reference electrode. Fluoride ions are added to the test solution as part of a fluoride compound.

The apparatus of the invention may further comprise: a sampling device operative to flow a predetermined volume of the etchant solution from an etchant container to the analysis cell; and a reagent device operative to flow a predetermined volume of a reagent solution comprising a predetermined concentration of a fluoride compound from a reagent reservoir to the analysis cell. The etchant container may be an etchant reservoir or a production etchant tank. Preferably, the sampling device and the reagent device are controlled by the computing device such that the silicon analysis of the invention may be performed automatically. By flowing the etchant solution at a predetermined etchant solution flow rate through the analysis cell and flowing the reagent solution at a predetermined reagent solution flow rate through the analysis cell, the silicon concentration in the etchant solution may be determined continuously.

The apparatus of the invention may further comprise: a means of rapidly cooling the predetermined volume of the etchant solution to a predetermined temperature so as to shorten the measurement time; and/or a means of measuring and/or controlling the temperature of the test solution so as to minimize and/or correct for the effects of temperature fluctuations on the potential measured for the fluoride ion specific electrode. Preferably, such temperature correction and control functions are performed automatically by the computing device.

The invention is useful for reducing the costs and improving the quality and yield of semiconductor IC chips by enabling accurate, rapid and cost-effective determination of the silicon concentration in silicon nitride etchant solutions. The steps of the method of the invention are simple to perform, involving standard addition of a fluoride compound to a sample of the etchant solution (preferably diluted with water) and measurement of the fluoride ion concentration in the resulting test solution, preferably via a fluoride ion specific electrode (ISE). A preferred apparatus of the invention, which basically comprises an analysis cell, a fluoride ISE, a reference electrode and a voltmeter, is simple, compact and inexpensive, and is readily amenable to on-line use and frequent or continuous measurement of the silicon concentration. The environmental impact of the silicon determination of the invention is small since only small amounts of the etchant solution and fluoride compound are required.

The invention enables the etch time for $Si_3N_4/SiO_2$ layers on silicon wafers to be adjusted to accurately take into account the effect of the silicon concentration in the etchant solution on the $Si_3N_4$ and $SiO_2$ etch rates. Accurate measurement of the silicon concentration according to the invention also enables etchant solutions to be replaced based on need rather than a time schedule so as to minimize costs and the amount of waste generated.

Further features and advantages of the invention will be apparent to those skilled in the art from the following detailed description, taken together with the accompanying drawings.

DETAILED DESCRIPTION OF THE INVENTION

Figure 1:
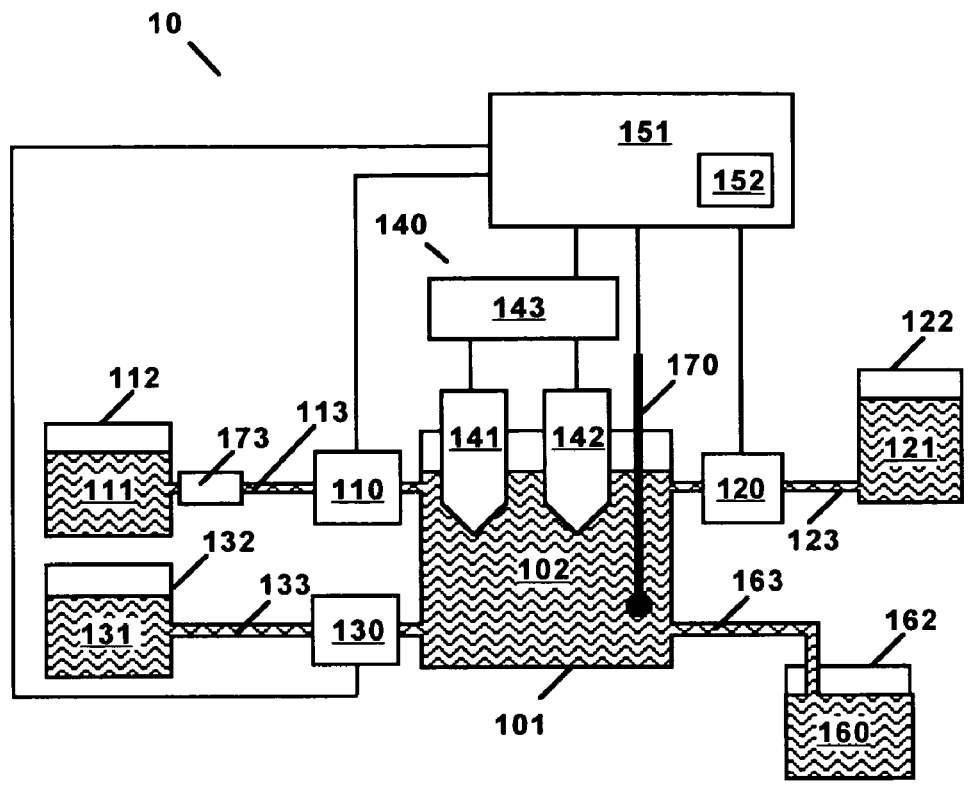
FIG. 1 schematically illustrates an apparatus of the invention for determining a silicon concentration in a phosphoric acid etchant solution.

Technical terms used in this document are generally known to those skilled in the art. The term "standard addition" generally means addition of a predetermined quantity of a species to a predetermined volume of a solution (a test solution, for example). The predetermined quantity may be a predetermined weight of the species or a predetermined volume of a standard solution containing the species. A "standard solution" comprises a precisely known concentration of a reagent used for a chemical analysis. The symbol "M" means molar concentration. Calibration data are typically handled as calibration curves or plots but such data may be tabulated and used directly, especially by a computer, and the terms "curve" or "plot" include tabulated data. Water used for solution preparation or dilution is preferably substantially pure water, deionized or distilled water, for example.

The invention provides a method and an apparatus suitable for determining the silicon concentration in an etchant solution. The invention may be applied to various etchant solutions but is particularly well-suited for analysis of silicon nitride etchant solutions comprising a high concentration of phosphoric acid. A typical silicon nitride etchant solution comprises 85% $H_3PO_4$ and is operated at 165° C. The method of the invention involves reacting substantially all of the silicon ions in the etchant solution with fluoride ions added in stoichiometric excess, and measuring the concentration of the unreacted fluoride ions, preferably via a fluoride ion specific electrode (ISE). The method of the invention may also be applied to analyze silicon in etchant solutions used to etch materials other than silicon nitride, silicon dioxide, for example.

The method of the invention for determining a silicon concentration in an etchant solution, comprises the basic steps of: providing a test solution comprising a predetermined volume of the etchant solution; adding a predetermined concentration of fluoride ions to the test solution; measuring a measured concentration of fluoride ions in the test solution; and determining the silicon concentration from the difference in the predetermined and the measured concentrations of fluoride ions in the test solution. The predetermined volume of the etching solution may be provided manually, using a syringe, a volumetric flask or a graduated cylinder, for example, or automatically, via an automatic syringe or a metering pump, for example. Fluoride ions may be added as part of any fluoride compound that tends to dissociate in aqueous solution, HF, LiF, NaF, KF, $NH_4HF_2$, $NH_4F$, and mixtures thereof, for example. The predetermined concentration of fluoride ions may be added to the test solution as part of a solid compound of known weight, or as a predetermined volume of a standard fluoride solution.

The measured concentration of fluoride ions in the test solution may be measured by any suitable means but is preferably measured using a fluoride ion specific electrode (ISE). In this case, the step of measuring the measured concentration of fluoride ions in the test solution comprises the steps of: placing a fluoride ion specific electrode (ISE) and a reference electrode in contact with the test solution, and measuring the potential of the fluoride ISE relative to the reference electrode. The fluoride ISE and the reference electrode may be separate electrodes or may be combined in a combination electrode.

It is understood by those skilled in the art that silicon is present in aqueous solutions in ionic form, the fundamental species being the silicate ion ($SiO_3^{2-}$) which tends to exist as the protonated species $HSiO_3^-$ and $H_2SiO_3$ in acidic solutions. However, since silicon forms a variety of complexes and the exact species formed by dissolution of silicon nitride in a phosphoric acid etchant solution at elevated temperature are unknown, the term "silicon concentration" is used to denote the total concentration of all silicon ions in a solution expressed in terms of the silicon weight per unit volume of the solution (ppmV). For determining the silicon concentration, the product of the reaction between silicon ions and fluoride ions is assumed to be the hexafluorosilicic ion ($SiF_6^{2-}$) formed by the overall reaction:

$$H_2SiO_3 + 6HF = H_2SiF_6 + 3H_2O$$

involving the dissociated HF species.

The term "fluoride ions" denotes "free" $F^-$ ions formed by dissociation of a fluoride compound in aqueous solution. For example, hydrofluoric acid (HF) dissociates according to:

$$HF = H^+ + F^- \qquad (1)$$

providing the free fluoride ions ($F^-$) that are detected by a fluoride ion specific electrode (ISE). Under ideal conditions, the potential (E) of a fluoride ISE is given by the well-known Nernst equation:

$$E = E_o - (2.303 RT/nF) \log [F^-] \qquad (2)$$

where $E_o$ is the standard equilibrium potential, R is the natural gas constant, T is the temperature (° K), n is the number of electrons transferred in the electrode reaction, F is faradays constant, and $[F^-]$ is the activity of fluoride ions. The value of 2.303 RT/nF is 59 mV/decade for a one-electron reaction at 25° C. Thus, were HF completely dissociated into $H^+$ and $F^-$ ion, a plot of the potential of a fluoride ISE versus log $[F^-]$ should be linear with a slope of 59 mV/decade. Note that fluorine in HF and other undissociated compounds or ions ($SiF_6^{2-}$ ion, for example) is not detected by the fluoride ISE.

In practice, Nernstian slopes for fluoride detected by a fluoride ISE typically deviate somewhat from the theoretical values (59 mV/decade) due to incomplete dissociation of the fluoride compound (HF, for example), variations in the concentrations of other species involved in the equilibrium ($H^+$ ion from phosphoric acid, for example), and/or non-ideal solution behavior (non-unity activity coefficients, for example). The potentials of fluoride ion specific electrodes and reference electrodes also exhibit some variability from electrode to electrode and tend to drift with time. Nonetheless, the potential response of the fluoride ion specific electrode in phosphoric acid etchant solutions, especially when diluted with water, tends to be sufficiently reproducible to provide a reliable measure of the fluoride concentration, and indirectly the silicon concentration.

According to the Nernst equation (Eq. 2), the potential of a fluoride ISE in a test solution is directly proportional to the temperature of the test solution. It is therefore preferable that the potential of the fluoride ISE in the test solution be measured at constant temperature, or be corrected for fluctuations in the temperature of the test solution. Such temperature corrections can be made using the Nernst equation (Eq. 2).

In a preferred embodiment, the method of the invention further comprises the step of: generating a calibration curve by measuring the potential of the fluoride ISE relative to the reference electrode at a predetermined calibration temperature in at least two calibration solutions having different predetermined concentrations of silicon added to a background electrolyte. The background electrolyte preferably comprises the same constituents at substantially the same concentrations (except for silicon) as the test solution. The background electrolyte for a typical silicon nitride etchant, for example, comprises phosphoric acid and fluoride ions.

In this embodiment, the silicon concentration in the test solution is determined by comparing the potential of the fluoride ISE measured for the test solution with the calibration curve. Preferably, the potential of the fluoride ISE is measured with the test solution at the calibration temperature, or is corrected for the difference in the temperature of the test solution and the calibration temperature (using the Nernst equation). In the latter case, the corrected potential is compared with the calibration curve. A preferred calibration curve is a plot of the fluoride ISE potential as a logarithmic function of the silicon concentration in the test solution. For this plot, the silicon concentration in the test solution can be read directly from the calibration curve.

In a preferred embodiment, the test solution further comprises a predetermined volume of water added to dilute the etchant in the test solution. Dilution of a phosphoric acid etchant used to etch silicon nitride has been found to improve the reproducibility and linearity of the fluoride ISE response. Preferably, the fluoride compound is dissolved in the added water to provide a standard fluoride ion solution such that the predetermined concentration of fluoride ions is added to the test solution as part of the predetermined volume of added water. Alternatively, at least a portion of the predetermined volume of water added to dilute the phosphoric acid in the test solution may be added as substantially pure water.

FIG. 1 schematically illustrates an apparatus 10 of the invention for determining a silicon concentration in an etchant solution 111, comprising: an analysis cell 101 containing a test solution 102 comprising a predetermined volume of etchant solution 111 and a predetermined concentration of fluoride ions; a means 110 of providing the predetermined volume of etchant solution 111 contained in an etchant container 112; a means 130 of adding the predetermined concentration of fluoride ions to test solution 102; a means 140 of measuring the concentration of fluoride ions in test solution 102; and a computing device 151 having a memory element 152 with a stored algorithm operative to effect, via appropriate mechanical and electrical interfacing, at least the basic steps of the method of the invention, comprising: providing test solution 102 comprising the predetermined volume of etchant solution 111; adding the predetermined concentration of fluoride ions to test solution 102; measuring a measured concentration of fluoride ions in test solution 102; and determining the silicon concentration in etchant solution 111 from the difference in the predetermined and the measured concentrations of fluoride ions in test solution 102. Analysis cell 101 may be of any suitable shape, including an open beaker or a closed cell with feedthroughs for the electrodes (as shown in FIG. 1), for example, and may comprise any suitable material, glass or a polyolefin plastic, for example.

Means 110 of providing the predetermined volume of etchant solution 111 contained in a etchant container 112 may comprise a syringe, a volumetric flask or a graduated cylinder, for example, for manual delivery, or an automatic syringe or a metering pump with associated plumbing and wiring, for example, for automatic delivery (as indicated in FIG. 1). Etchant container 112 may be a production etchant tank or an etchant reservoir. For automatic delivery of etchant solution 111, means 110 is connected to a pipe 113 running between etchant container 112 and analysis cell 101.

Fluoride ions may be added to test solution 102 as part of any suitable fluoride compound that tends to dissociate in aqueous solution, HF, LiF, NaF, KF, $NH_4HF_2$, $NH_4F$, and mixtures thereof, for example. The predetermined concentration of fluoride ions may be added to test solution 102 as part of a solid compound of known weight, or as a predetermined volume of a standard fluoride solution 131 contained in a reagent reservoir 132 (as indicated in FIG. 1). Addition of the predetermined concentration of fluoride ions via a standard fluoride solution is preferred since reagents are generally more easily handled as liquids, and dilution of the etchant solution tends to provide more reproducible fluoride ISE measurements in any case.

For delivering a predetermined volume of fluoride standard solution 131 from reagent reservoir 132 to test solution 102 in analysis cell 101, means 130 may comprise a syringe, a volumetric flask or a graduated cylinder, for example, for manual delivery, or an automatic syringe or a metering pump with associated plumbing and wiring, for example, for automatic delivery. For automatic delivery of reagent solution 131, means 130 is connected to a pipe 133 running between reagent reservoir 132 and analysis cell 101.

The predetermined concentration of added fluoride ions and a predetermined dilution ratio of etchant solution 111 in test solution 102 may be provided by addition of any suitable combination of solid fluoride compound, standard fluoride solution, and pure water. Pure water may be added, for example, so that the reagent solution can be provided as a concentrate to minimize shipping and handling costs. For addition of pure water, the apparatus of the invention may further comprise: a dilution device 120 operative to provide metered flow of water 121 from a water reservoir 122 to the analysis cell 101 so as to provide a predetermined volume fraction of water in the test solution. Dilution device 120 may comprise a syringe, a volumetric flask or a graduated cylinder, for example, for manual delivery, or an automatic syringe or a metering pump with associated plumbing and wiring, for example, for automatic delivery (as indicated in FIG. 1). For automatic delivery of water 121, dilution device 120 is connected to a pipe 123 running between water reservoir 121 and analysis cell 101. Preferably, computing device 151 with the stored algorithm is further operative to control dilution device 120.

Means 140 of measuring the concentration of fluoride ions in test solution 102 preferably comprises a fluoride ion specific electrode 141 and a reference electrode 142 in contact with test solution 102, and a voltmeter 143 for measuring the potential between the two electrodes. Suitable reference electrodes and fluoride ion specific electrodes are well-known in the art and are available commercially. Typical reference electrodes include the silver-silver chloride electrode (SSCE), saturated calomel electrode (SCE), mercury-mercury sulfate electrode, for example. A double junction may be used for one or both electrodes to minimize contamination of the electrode solution by etchant solution species (which may cause drift in the electrode potential). Fluoride ion specific electrode 141 and reference electrode 142 may be separate electrodes or may be combined in a combination electrode.

After a fluoride ISE measurement is completed, test solution 102 is preferably flowed via waste pipe 163 into waste container 162. Between silicon determinations, analysis cell 101 is preferably rinsed with water. Analysis cell 101 may be rinsed using water provided by dilution device 120 or by a separate rinse system (not shown). Waste 160 is disposed.

Fluoride ISE calibrations and measurements should be performed at a constant temperature, preferably at or near room temperature, and/or fluoride ISE potentials should be corrected for significant variations in the temperature of test solution 102. Preferably, the apparatus of the invention further comprises: a temperature sensor 170 for measuring the temperature of test solution 102. Temperature sensor 170 may be of any suitable type, including a thermometer, a thermocouple (as indicated in FIG. 1), a thermistor, or an NIR spectrometer, for example. Preferably, computing device 151 is further operative to acquire temperature data from the temperature sensor 170 and correct the potentials measured for fluoride ISE 141 for temperature effects so as to provide a more accurate determination of the fluoride concentration in test solution 102.

Since silicon nitride etchant solutions operate at high temperature (>150° C.), a means for rapidly cooling the predetermined volume of etchant solution 111 can significantly shorten the analysis time. Any suitable cooling means may be used. For example, as indicated in FIG. 1, etchant solution 111 flowed from etchant tank 112 to analysis cell 101 may be passed through a cooling device 173, which may comprise a jacketed portion of pipe 113 or a heat radiator device, for example.

The apparatus of the invention preferably includes a means of controlling the temperature of test solution 102 to minimize errors in the measured concentration of fluoride ions in test solution 102. Suitable means of controlling the temperature of a liquid are well-known in the art. For example, a hot plate or an immersion heater with feedback from a temperature sensor may be used to control the temperature of a liquid in an analysis cell. A preferred means of controlling the temperature of test solution 102 is to pass water or another heat exchange liquid from a circulator/controller (or another constant temperature source) through a cooling jacket on analysis cell 101 (not shown).

Computing device 151 may comprise a computer with integrated components, or may comprise separate components, a microprocessor and a memory device that includes memory element 152, for example. Memory element 152 may be any one or a combination of available memory elements, including a computer hard drive, a microprocessor chip, a read-only memory (ROM) chip, a programmable read-only memory (PROM) chip, a magnetic storage device, a computer disk (CD) and a digital video disk (DVD), for example. Memory element 152 may be an integral part of computing device 151 or may be a separate device.

DESCRIPTION OF A PREFERRED EMBODIMENT

A preferred embodiment of the apparatus of the invention for determining a silicon concentration in an etchant solution comprises: an analysis cell containing a test solution comprising a predetermined volume fraction of the etchant solution and a predetermined volume fraction of a reagent solution comprising a predetermined concentration of fluoride ions; a sampling device operative to provide metered flow of the etchant solution through a sample pipe from an etchant tank to the analysis cell so as to provide the predetermined volume fraction of the etchant solution; a reagent device operative to provide metered flow of a reagent solution through a reagent tube from a reagent reservoir to the analysis cell so as to provide the predetermined volume fraction of the reagent solution; a means of measuring the concentration of fluoride ions in the test solution, comprising a fluoride ion specific electrode (ISE) in contact with the test solution in the analysis cell, a reference electrode in contact with the test solution in the analysis cell, and a voltmeter for measuring the potential of the fluoride ISE relative to the reference electrode; a temperature sensor for measuring the temperature of the test solution; and a computing device having a memory element with a stored algorithm operative to effect, via appropriate interfacing, the steps of a preferred method of the invention.

With reference to paragraph [0042], the preferred method comprises the steps of: generating a calibration curve by measuring the potential of the fluoride ISE relative to the reference electrode at a predetermined calibration temperature in at least two calibration solutions having different predetermined concentrations of silicon added to a background electrolyte; providing the test solution by flowing the predetermined volume fraction of the etchant solution and the predetermined volume fraction of the reagent solution into the analysis cell; measuring the temperature of the test solution; measuring the potential of the fluoride ISE relative to the reference electrode in the test solution; correcting the potential measured for the fluoride ISE in the test solution for the effect of the difference between the temperature measured for the test solution and the calibration temperature to provide a corrected measured potential; and determining the silicon concentration in the test solution by comparing the corrected measured potential of the fluoride ISE in the test solution with the calibration curve. Preferably, the preferred embodiment of the apparatus of the invention further comprises: a means of maintaining the test solution in the analysis cell at a predetermined temperature.

Figure 2:
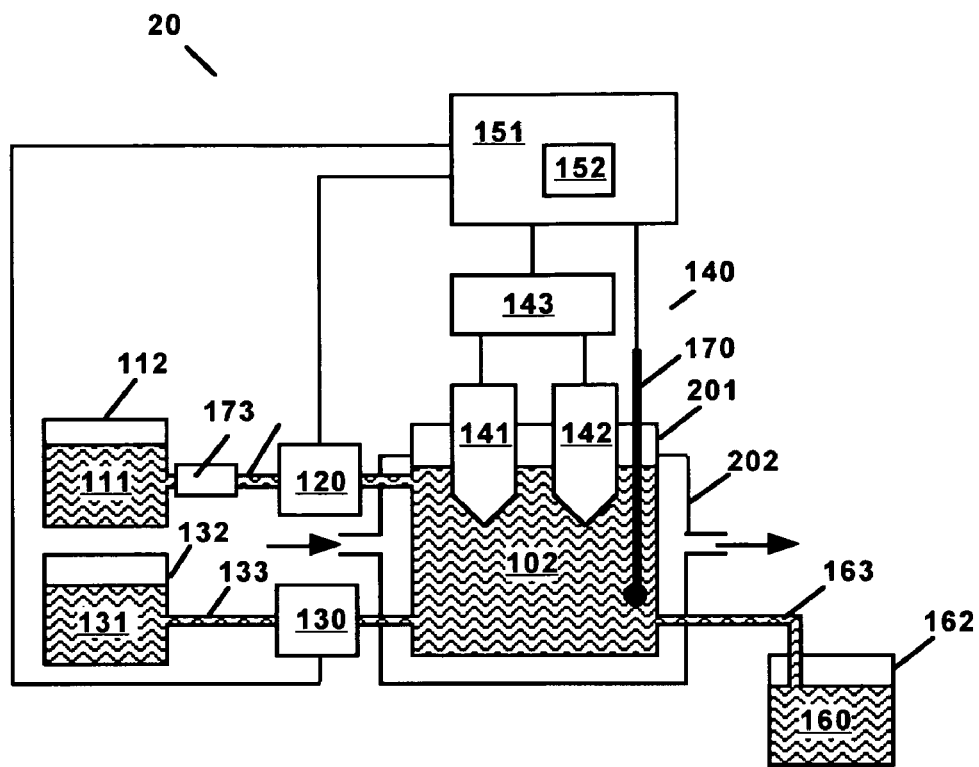
FIG. 2 is a schematic representation of a preferred apparatus of the invention.

FIG. 2 schematically illustrates a preferred apparatus 20 of the invention for determining a silicon concentration in an etchant solution 111. This preferred apparatus is the same as that depicted in FIG. 1 except that dilution device 120 of FIG. 1 has been omitted, and a cooling jacket 202 is included on analysis cell 201 for maintaining test solution 102 at a predetermined temperature.

The efficacy of the invention for determining the silicon concentration in silicon nitride etchant solutions was demonstrated for a phosphoric acid etchant solution (85 wt. % $H_3PO_4$) containing various predetermined concentrations of silicon (20, 50 and 100 ppmV) added by standard addition of 5000 ppmV $Na_2SiO_3.9H_2O$ solution. Test solutions were prepared by addition of 0.15 mL of a reagent solution comprising 49.5 wt. % HF to a predetermined volume (25.00 mL) of the etchant solution, which provided an approximately ten-fold stoichiometric excess of fluoride ions to silicon ions in the test solution. For one set of determinations, the test solution was diluted 1:1 with distilled water. The fluoride ion concentration in the test solutions was measured at room temperature using a combination fluoride ion specific electrode/silver-silver chloride reference electrode (4.0 M KCl). The silicon concentration in the test solutions was calculated by assuming that the product of the reaction between silicon ions and fluoride ions was hexafluorosilicic acid ($H_2SiF_6$).

Figure 3:
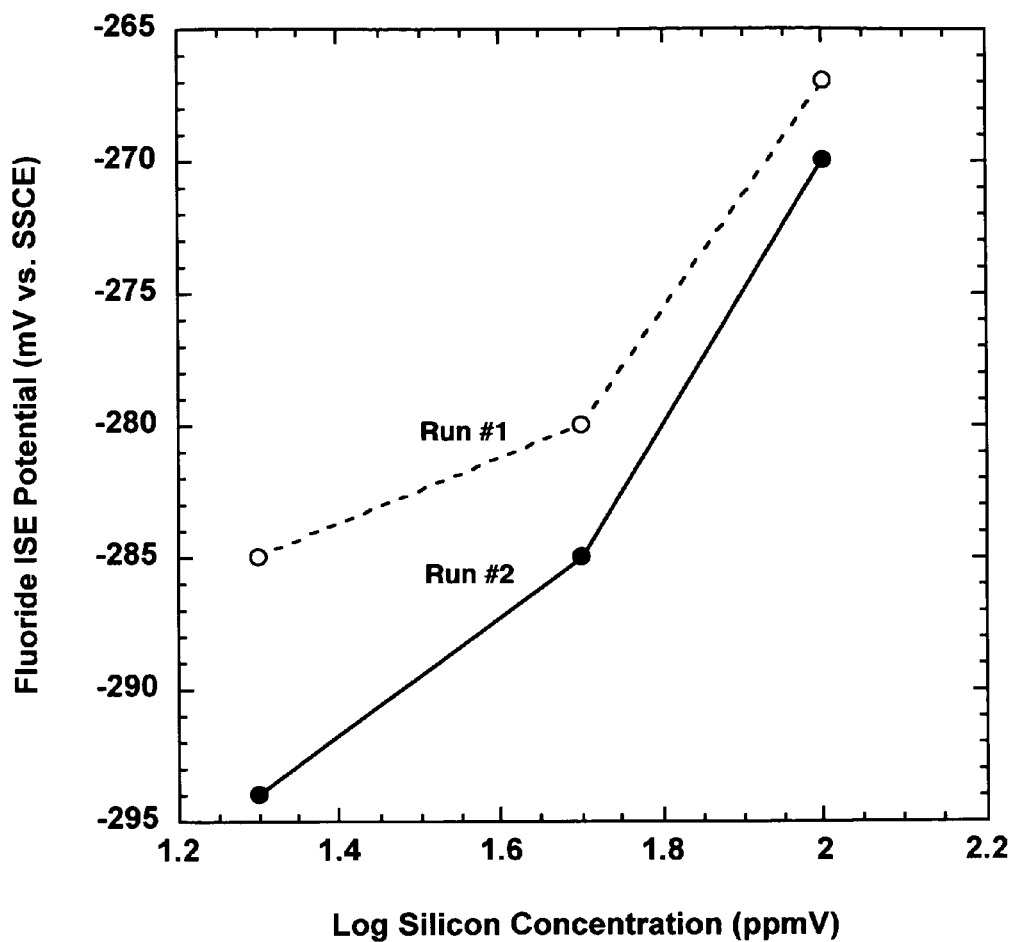
FIG. 3 shows plots for two experimental runs of the potential of a fluoride ISE versus the logarithm of the silicon concentration in undiluted 85 wt. % phosphoric acid etchant solution.

Table 1 and FIG. 3 summarize the results for measurements (two runs) of the potential of the fluoride ion specific electrode (ISE) as a function of the silicon concentration in the 85 wt. % phosphoric acid etchant solution. For these undiluted test solutions, response of the fluoride ISE was slow and reproducibility was poor, probably due at least in part to the high viscosity of the phosphoric acid solution at room temperature. As evident from FIG. 3, the logarithmic dependence of the fluoride ISE potential on the silicon concentration, predicted by the Nernst equation if the silicon concentration is directly proportional to the fluoride concentration, is not observed for the undiluted etchant solution.

TABLE 1

Silicon Analysis Results for
Undiluted Phosphoric Acid Etchant Solutions

| Added Si | Fluoride ISE Voltage (mV) | |
|---|---|---|
| (ppmV) | Run #1 | Run #2 |
| 20 | −294 | −285 |
| 50 | −285 | −280 |
| 100 | −270 | −267 |

Figure 4:
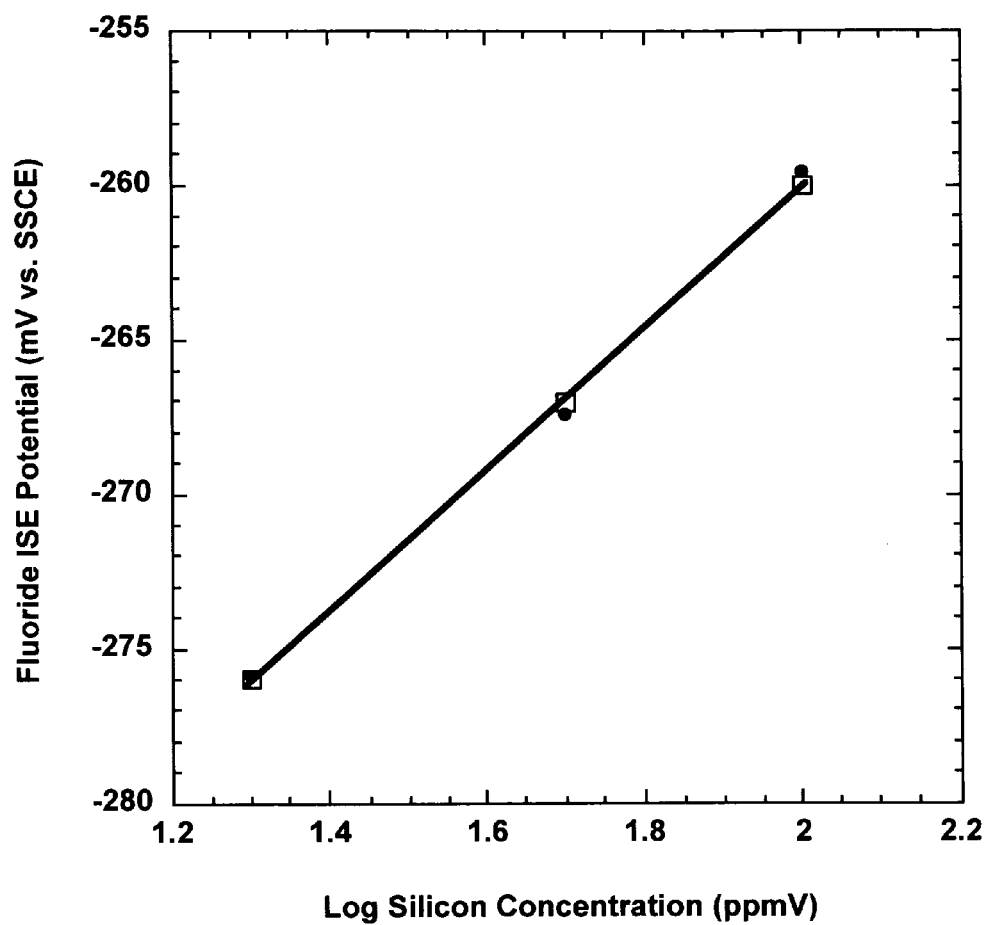
FIG. 4 shows plots for two experimental runs of the potential of a fluoride ISE versus the logarithm of the silicon concentration in 85 wt. % phosphoric acid etchant solution diluted 1:1 with deionized water.

Table 2 and FIG. 4 summarize the results for measurements (two runs) of the potential of the fluoride ion specific electrode (ISE) as a function of silicon concentration in the phosphoric acid etchant solution diluted 1:1 with deionized water. For the diluted solution, response of the fluoride ISE was much faster, reproducibility was very good, relative standard deviation (RSD) was 2% or less, and accuracy was generally within ±4 percent. Furthermore, as evident from FIG. 3, the fluoride ISE potential for the diluted etchant solution exhibits the logarithmic dependence on the silicon concentration predicted by the Nernst equation.

TABLE 2

Silicon Analysis Results
for 1:1 Diluted Phosphoric Acid Etchant Solutions

| Added Si | FISE Voltage (mV) | | Measured Si (ppmV) | | | |
|---|---|---|---|---|---|---|
| (ppmV) | Run #1 | Run #2 | Run #1 | Run #2 | Accuracy | RSD |
| 20 | −276 | −276 | 20.4 | 20.2 | −1% | 1% |
| 50 | −267 | −267 | 47.9 | 47.9 | 4% | 0% |
| 100 | −260 | −260 | 102.5 | 105.7 | −4% | 2% |

The preferred embodiments of the present invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

We claim:

1. A method for determining a silicon concentration in an etchant solution, comprising the steps of:

providing a test solution comprising a predetermined volume of the etchant solution;

adding a predetermined concentration of fluoride ions to the test solution;

measuring a measured concentration of fluoride ions in the test solution; and determining the silicon concentration from the difference in the predetermined and the measured concentrations of fluoride ions in the test solution, wherein fluoride ions are added to the test solution as part of a fluoride compound.

2. The method of claim 1, wherein the fluoride compound is selected from the group consisting of HF, LiF, NaF, KF, $NH_4HF_2$, $NH_4F$, and mixtures thereof.

3. The method of claim 1, wherein the test solution further comprises a predetermined volume of water added to dilute the etchant solution.

4. The method of claim 1, wherein the predetermined concentration of fluoride ions is added to the test solution via a standard fluoride solution comprising a predetermined concentration of the fluoride compound dissolved in water.

5. The method of claim 1, wherein the etchant solution comprises phosphoric acid.

6. The method of claim 1, wherein the step of measuring the measured concentration of fluoride ions in the test solution comprises the steps of
 placing a fluoride ion specific electrode (ISE) and a reference electrode in contact with the test solution, and
 measuring a potential of the fluoride ISE relative to the reference electrode,
 wherein the fluoride ISE and the reference electrode may be separate electrodes or may be combined in a combination electrode.

7. The method of claim 6, further comprising the step of:
 generating a calibration curve by measuring the potential of the fluoride ISE relative to the reference electrode at a predetermined calibration temperature in at least two calibration solutions having different predetermined concentrations of silicon added to a background electrolyte,
wherein the silicon concentration in the test solution is determined by comparing the potential of the fluoride ISE measured for the test solution with the calibration curve.

8. The method of claim 7, further comprising the steps of:
measuring a temperature of the test solution; and
correcting the potential measured for the fluoride ISE for the effect of the difference in the temperature of the test solution and the predetermined calibration temperature.

* * * * *